United States Patent
Dong et al.

(10) Patent No.: US 10,253,026 B2
(45) Date of Patent: Apr. 9, 2019

(54) PROCESS FOR THE PREPARATION OF (R)-8-(3-AMINOPIPERIDIN-1-YL)-7-(BUT-2-YN-1-YL)-3-METHYL-1-((4-METHYLQUINA-ZOLIN-2-YL)METHYL)-3,7-DIHYDRO-1H-PURINE-2,6-DIONE

(71) Applicant: Boehringer Ingelheim International GmbH, Ingelheim am Rhein (DE)

(72) Inventors: Weitong Dong, Shanghai (CN); Yao Huang, Shanghai (CN); Shengmin Su, Shanghai (CN); Yongfen Sun, Shanghai (CN); Pengtao Zhang, Shanghai (CN)

(73) Assignee: Boenringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/737,760

(22) PCT Filed: Jun. 24, 2016

(86) PCT No.: PCT/EP2016/064692
§ 371 (c)(1),
(2) Date: Dec. 19, 2017

(87) PCT Pub. No.: WO2016/207364
PCT Pub. Date: Dec. 29, 2016

(65) Prior Publication Data
US 2018/0179207 A1  Jun. 28, 2018

(30) Foreign Application Priority Data
Jun. 25, 2015 (WO) ............... PCT/CN2015/082288

(51) Int. Cl.
C07D 473/04 (2006.01)
(52) U.S. Cl.
CPC ................... *C07D 473/04* (2013.01)
(58) Field of Classification Search
CPC .................................................. C07D 473/04
USPC ....................................................... 544/272
See application file for complete search history.

(56) References Cited

U.S. PATENT DOCUMENTS 7,820,815 B2  10/2010  Pfrengle et al.
2006/0142310 A1  6/2006  Pfrengle et al.

FOREIGN PATENT DOCUMENTS

| CN | 103450201 A | 12/2013 |
| DE | 102004054054 A1 | 5/2006 |
| WO | 13098775 A1 | 7/2013 |
| WO | WO 16/207364 | * 12/2016 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
International Search Report and Written opinion, for PCT/EP2016064692, dated Aug. 2, 2016.
Eckardt, 8-(3-(R)-Aminopiperidin-1-yl)-7-but-2-ynyl-3-methyl-1-(4-methyl-quinazolin-2-ylmethyl)-3,7-dihydropurine-2,6-dione (BI 1356), a highly potent, selective, long-acting, and orally bioavailable DPP-4 inhibitor for the treatment of Type 2 Diabetes, J. Med. Chem, 2007, vol. 50, p. 6450-6453.
Abstract for CN103450201 cited herein.
International Report on Patentability, ISA 237, for PCT/EP2016/064692, dated Jan. 4, 2018.

* cited by examiner

*Primary Examiner* — Douglas M Willis
(74) *Attorney, Agent, or Firm* — David L. Kershner

(57) ABSTRACT

This invention relates to a method for preparation of a xanthine-based compound of formula (I):

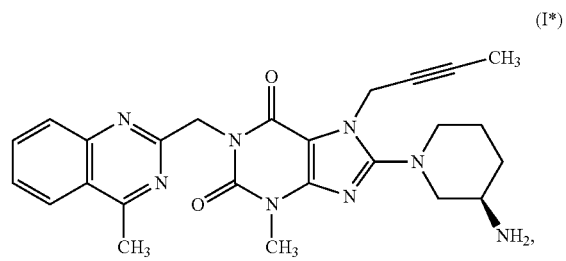

(I*)

as well as to intermediates useful in such preparation.

9 Claims, No Drawings

PROCESS FOR THE PREPARATION OF (R)-8-(3-AMINOPIPERIDIN-1-YL)-7-(BUT-2-YN-1-YL)-3-METHYL-1-((4-METHYLQUINAZOLIN-2-YL)METHYL)-3,7-DIHYDRO-1H-PURINE-2,6-DIONE

FIELD OF THE INVENTION

This invention relates to a method for preparation of a xanthine-based pharmaceutically active ingredient, namely Linagliptin, as well as to intermediates useful in such preparation.

BACKGROUND OF THE INVENTION

1-[(4-Methyl-quinazolin-2-yl)methyl]-3-methyl-7-(2-butyn-1-yl)-8-(3-(R)-amino-piperidin-1-yl)-xanthine, whose international nonproprietary name is Linagliptin, has the following structure as shown below:

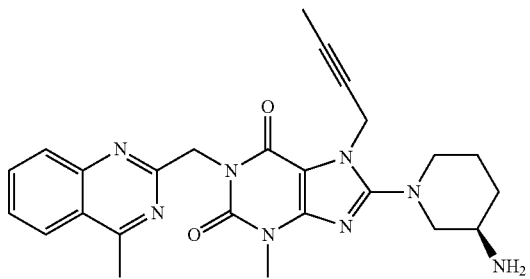 [SMILES: CC#CCn1c(N2CCC[C@@H](N)C2)nc2c1c(=O)n(Cc1nc(C)c3ccccc3n1)c(=O)n2C]

Up to now, several synthetic routes to synthesize the molecule have been described by several references.

For example, a process for the preparation of Linagliptin is disclosed in the references WO 2004/018468 and WO 2006/048427.

The reference WO 2014/059938 describes a further process for preparation of Linagliptin involving a phase transfer catalyst and using protected (R)-piperidine-3-amine derivatives. The process of WO 2014/059938 requires an amine protecting group, such as tert-butyloxy carbonyl (Boc) protection and de-protection of the intermediates used in the late stage of the synthesis process.

The reference WO 2013/098775 describes a further process for preparation of Linagliptin: (R)-piperidine-3-amine (or its dihydrochloride) is said to be used directly to react with 1-[(4-methyl-quinazolin-2-yl)methyl]-3-methyl-7-(2-butyn-1-yl)-8-bromo-xanthine in the presence of a suitable base (particularly $K_2CO_3$) in an inert organic solvent (particularly DMF or MIBK) to give Linagliptin. However, the reference WO 2013/098775 only discloses to use the 1-[(4-methyl-quinazolin-2-yl)methyl]-3-methyl-7-(2-butyn-1-yl)-8-bromo-xanthine as intermediate.

It is desired to find a further process for the preparation of Linagliptin which is suitable for large scale production, particularly for pharmaceutical purposes.

BRIEF SUMMARY OF THE INVENTION

It has now been found that the process, which is described in greater detail herein, does not require any amine protecting group and provides an efficient, short, robust and scalable method for preparation of Linagliptin and is particularly suitable for the preparation of pure Linagliptin such as for pharmaceutical and medical purposes.

Accordingly, the present invention relates to a process for preparation of Linagliptin, intermediates useful in such process, and use of the process and the intermediates for preparation of Linagliptin for use as medicament.

The invention further relates to a process for preparation of a pharmaceutical composition of Linagliptin, said process comprising i) preparing Linagliptin according to a process as described herein, and ii) combining Linagliptin with one or more pharmaceutically acceptable excipients in order to form the pharmaceutical composition.

DETAILED DESCRIPTION OF THE INVENTION

Based on our studies, besides Br as a leaving group, Cl or I can serve as the leaving groups in the 8-position of 1-[(4-methyl-quinazolin-2-yl)methyl]-3-methyl-7-(2-butyn-1-yl)-xanthine and their corresponding substrates, namely 1-[(4-methyl-quinazolin-2-yl)methyl]-3-methyl-7-(2-butyn-1-yl)-8-chloro-xanthine and 1-[(4-methyl-quinazolin-2-yl)methyl]-3-methyl-7-(2-butyn-1-yl)-8-iodo-xanthine, can be directly reacted with piperidine-3-amine [particularly (R)-piperidine-3-amine] or a salt thereof (such as the dihydrochloride salt), preferably (R)-piperidine-3-amine dihydrochloride, in the presence of a suitable base (such as an inorganic or organic base, e.g. $Na_2CO_3$ (sodium carbonate), $K_2CO_3$ (potassium carbonate), $NaHCO_3$ (sodium bicarbonate) or $KHCO_3$ (potassium bicarbonate)) in a suitable solvent (such as an organic or aqueous solvent, or mixtures of solvents, particularly an aprotic polar solvent, e.g. NMP (N-methyl-2-pyrrolidone), DMSO (dimethyl sulfoxide), DMAc (N,N-dimethylacetamide) or DMF (N,N-dimethylformamide)) to give Linagliptin with good yield and purity.

A method for preparing Linagliptin is outlined in the following SCHEME 1 involving the coupling reaction according to the present invention.

SCHEME 1

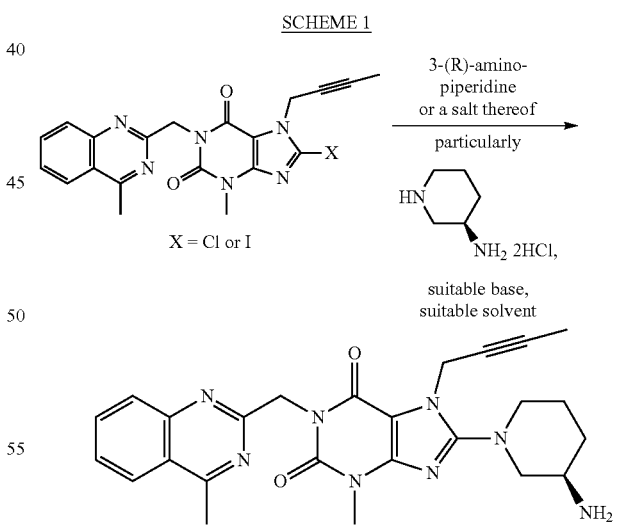

In certain more detailed embodiments of the invention, the present invention relates to the processes, methods and/or the individual process steps and/or the individual reaction conditions substantially as described by way of illustrative example in the following.

A process for preparing Linagliptin is outlined in the following SCHEME 2. In one embodiment, the present invention is directed to the multi-step synthetic method for preparing Linagliptin as substantially set forth in SCHEME 2 below. In other embodiments, the invention is directed to each of the individual steps of SCHEME 2 and any combination of two or more successive steps of SCHEME 2. The invention is also directed to the intermediate compounds, e.g. as set forth in SCHEME 2.

In more detailed example, the synthesis (SCHEME 2) may start with alkylation of 3-methyl-3,7-dihydro-purine-2,6-dione (7) for example with methanesulfonic acid but-2-ynyl ester (8) in the presence of a suitable base and a suitable solvent, such as in the presence of KHCO₃ in NMP to give Compound 9 with around 94% yield. Compound 9 may then be chlorinated for example by NCS such as in DMF to afford Compound 10 with around 83% yield. Alternatively, the chlorination may also be carried out in NMP, which makes one pot reaction from Compound 7 to Compound 10 possible. Then, Compound 10 may be reacted with 2-chloromethyl-4-methyl-quinazoline (11) in the presence of a suitable base and a suitable solvent, such as in the presence of Na₂CO₃ in NMP to give 7-but-2-ynyl-8-chloro-3-methyl-1-(4-methyl-quinazolin-2-ylmethyl)-3,7-dihydro-purine-2,6-dione (12) in 78% yield.

The coupling reaction of Compound 12 with (R)-3-aminopiperidine dihydrochloride (13) to form Linagliptin can be worked with different bases, like Na₂CO₃, NaHCO₃, or KHCO₃. For this coupling reaction, different kind of aprotic polar solvents can be used, including but not limited to NMP, DMSO, or DMF. The study shows that the combination of using NaHCO₃ as base and NMP as solvent offers the best results in terms of conversion and cleanness of reaction profile. Finally, after purification, e.g. by recrystallization such as in toluene, Linagliptin is obtained in 77% yield with 99.2% purity.

SCHEME 2

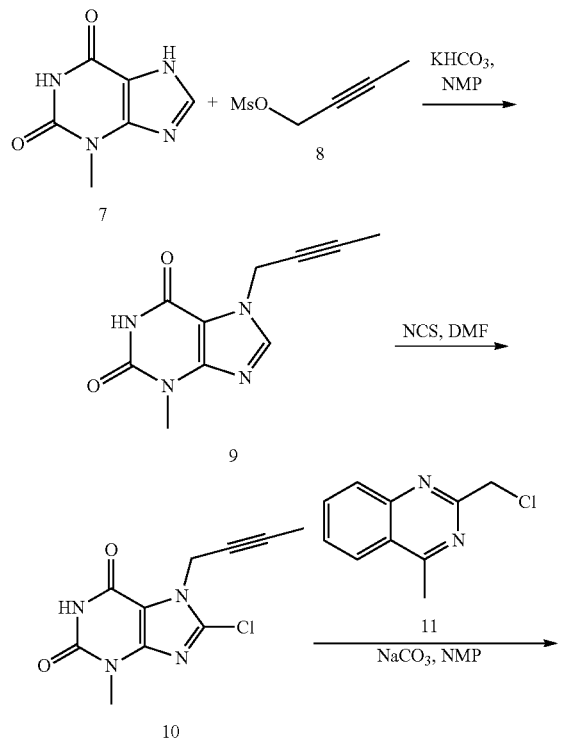

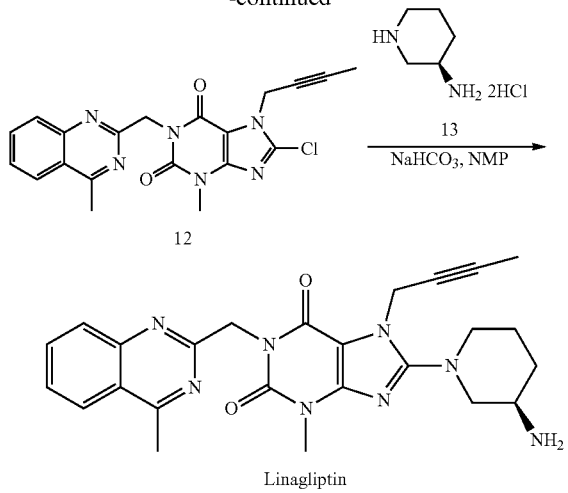

Another process for preparing Linagliptin is outlined in the following SCHEME 3. In one embodiment, the present invention is directed to the multi-step synthetic method for preparing Linagliptin as substantially set forth in SCHEME 3 below. In other embodiments, the invention is directed to each of the individual steps of SCHEME 3 and any combination of two or more successive steps of SCHEME 3. The invention is also directed to the intermediate compounds, e.g. as set forth in SCHEME 3.

In more detailed example, the iodide analogue (17) may be used for the direct coupling with (R)-3-aminopiperidine dihydrochloride (13) to prepare Linagliptin (SCHEME 3).

The synthesis may start with iodination of 3-methyl-3,7-dihydro-purine-2,6-dione (7) for example with NIS to give Compound 14 with around 91% yield, which may be followed by alkylation for example with 1-bromo-2-butyne (15) in the presence of a suitable base and a suitable solvent, such as in NMP in the presence of Na₂CO₃ to give Compound 16 in 97% yield. Then, Compound 16 may be reacted with 2-chloromethyl-4-methyl-quinazoline (11) in the presence of a suitable base and a suitable solvent, such as in presence of Na₂CO₃ in NMP to give Compound 17 in 65% yield.

The coupling reaction of Compound 17 with (R)-3-aminopiperidine dihydrochloride (13) to form Linagliptin can be worked in different kind of high polar solvents, like NMP, DMSO, DMAc, or DMF. Also, different kinds of bases can be used for this reaction, including but not limited to K₂CO₃, Na₂CO₃, NaHCO₃, or KHCO₃. Our study shows that the combination of DMSO as solvent and NaHCO₃ as base offers the best results in terms of the reaction conversion and cleanness of reaction profile. Finally, after purification, e.g. by column chromatography, Linagliptin is obtained in 54% yield with 99.0% purity.

SCHEME 3

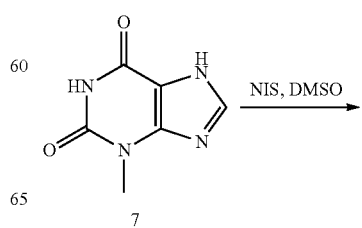

In certain embodiments, the present invention relates to an indicated intermediate or final compound in isolated form, such as e.g. in solid, amorphous, lyophilized or crystalline form.

In certain embodiments, the present invention relates to an indicated intermediate or final compound in solution form (such as e.g. present in a reaction solvent).

Further, the present invention relates to an indicated intermediate or final compound obtainable or obtained by a process or method according to the present invention.

In an embodiment, the present invention relates to Linagliptin isolated (such as e.g. crystallized) from the (reaction) solvents mentioned herein, such as e.g. toluene.

Accordingly, the invention further relates to the following particular Embodiments 1-10:

1. A method of preparing a compound of formula (I), said method comprising
reacting a compound of formula (II)

in which X is iodine or chlorine,
with
3-aminopipderidine of formula (III), or an enantiomer thereof, The alkylation reaction of Compound 7 or Compound 14 to prepare Compound 9 or Compound 16, respectively, can be represented as below. Based on our studies, the leaving group X used can be either of Br, I, OMs, or OTs in this reaction.

or a salt thereof,
optionally in the presence of a suitable base,
optionally in the presence of a suitable solvent,
to form the compound of formula (I).

2. The method according to Embodiment 1, wherein the compound of formula (I) has the following formula (I*):

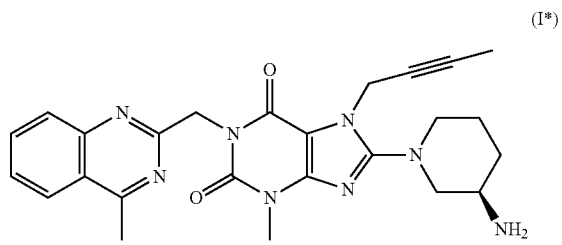 [SMILES: CC#CCn1c(N2CCC[C@@H](N)C2)nc2c1c(=O)n(Cc1nc(C)c3ccccc3n1)c(=O)n2C]

3. The method according to Embodiment 1 or 2, wherein the 3-aminopipderidine of formula (III) used in the reaction is

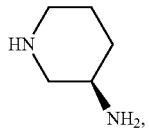

or a salt thereof, preferably

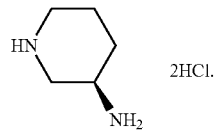

4. The method according to Embodiment 1, 2 or 3, wherein the suitable base is $Na_2CO_3$, $K_2CO_3$, $NaHCO_3$ or $KHCO_3$.
5. The method according to Embodiment 1, 2, 3 or 4, wherein the suitable solvent comprises NMP, DMSO, DMAc or DMF.
6. The method according to Embodiment 1, 2, 3, 4 or 5, wherein X is Cl.
7. The method according to Embodiment 1, 2, 3, 4 or 5, wherein X is Cl, the suitable base is $NaHCO_3$ and the suitable solvent is NMP.
8. The method according to Embodiment 1, 2, 3, 4 or 5, wherein X is I.
9. The method according to Embodiment 1, 2, 3, 4 or 5, wherein X is I, the suitable base is $NaHCO_3$ and the suitable solvent is DMSO.
10. The method according to any one of Embodiments 1 to 9, wherein the reaction is conducted at elevated reaction temperature, such as from 20° C. to 120° C., preferably 40° C. to 110° C.
11. The method according to any one of Embodiments 1 to 10, further comprising (re-)crystallizing the compound of formula (I) from a suitable solvent (e.g. toluene) or mixture of solvents.

The intermediates and final compounds of the invention may be obtained using methods of synthesis known in principle, or analogously or similarly to known procedures. Preferably, the intermediates involved and the final compounds may be obtained by the following methods according to the invention which are described in more detailed example herein after.

The process steps may be performed substantially as described herein by way of example. A process or method of this invention may comprise one or more steps of converting and/or reacting the mentioned intermediates with the appropriate reaction partners, suitably under conditions as disclosed herein (e.g. by using the indicated reagents and/or solvents and/or temperatures, etc.).

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by gas chromatography (GC), High Pressure Liquid Chromatography (HPLC) or Thin Layer Chromatography, if desired.

Synthetic Examples

In order that this invention would be more fully understood, the following examples are set forth. These examples are for the purpose of illustrating preferred (independent or dependent) embodiments of this invention, and are not to be construed as limiting the scope of the invention in any way.

Example 1: Preparation of 7-but-2-ynyl-3-methyl-3,7-dihydro-purine-2,6-dione (9)

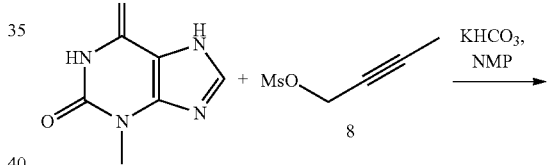

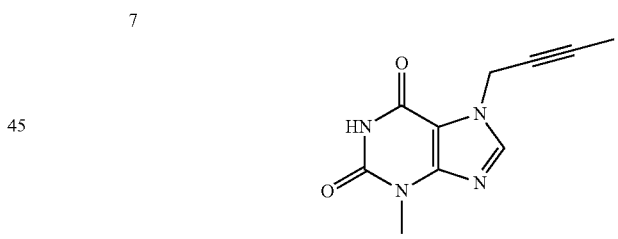

To a suspension of 20.0 g of 3-methyl-3,7-dihydro-purine-2,6-dione (7) and 13.2 g of $KHCO_3$ in 140 mL of NMP at 50° C., was charged a solution of 20.5 g of methanesulfonic acid but-2-ynyl ester (8) in 60 mL of NMP in 15 min. The reaction mixture was stirred at 50° C. for 7.5 h. Then, a total of 400 mL of water was added dropwise. The reaction mixture was cooled down to room temperature and stirred for 1 h. The product was collected by filtration and washed with 200 mL of water, then dried under vacuum. A total of 24.76 g (yield 94%) of Compound 9 was obtained as white solid with 97.6% HPLC purity. $^1$H NMR (500 MHz, $D_2O$): δ 7.46 (s, 1H), 4.61 (d, 3H, J=2.0 Hz), 3.03 (s, 3H), 1.57 (t, 3H, J=2.0 Hz); $^{13}$C NMR (125 MHz, $D_2O$): δ 164.87, 159.51, 149.98, 139.86, 108.56, 84.33, 71.44, 36.52, 29.22, 2.52; Mass (m/z): 219.1 (M+H)$^+$, 241.1 (M+Na)$^+$.

Example 2: Preparation of 7-but-2-ynyl-8-chloro-3-methyl-3,7-dihydro-purine-2,6-dione (10)

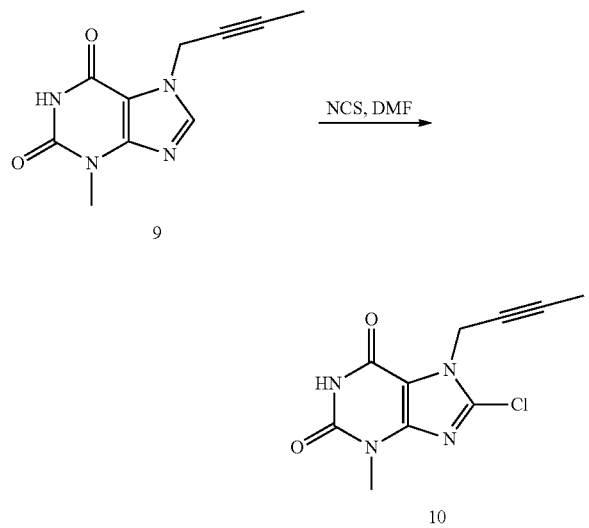

To a solution of 24.5 g of 7-but-2-ynyl-3-methyl-3,7-dihydro-purine-2,6-dione (9) in 245 mL of DMF, was charged a total of 20.6 g of NCS (N-chlorosuccinimide). The reaction mixture was stirred at 70° C. (internal temperature) for 4 h and then cooled down to 50° C. A total of 368 mL of water was added dropwise to the reaction mixture. The resulting suspension was cooled down to room temperature and stirred for 30 min.

The product was collected by filtration and washed with 100 mL of water, then dried under vacuum. A total of 23.4 g (yield 83%) of Compound 10 was obtained as light brown solid with 97.0% HPLC purity. $^1$H NMR (500 MHz, DMSO-$d_6$): δ 7.46 (s, 1H), 4.61 (d, 3H, J=2.0 Hz), 3.03 (s, 3H), 1.57 (t, 3H, J=2.0 Hz); $^{13}$C NMR (125 MHz, DMSO-$d_6$): δ 153.96, 150.42, 148.13, 137.56, 107.07, 81.88, 72.15, 35.37, 28.53, 2.97; Mass (m/z): 253.1 (M+H)$^+$, 275.0 (M+Na)$^+$.

Example 3: Preparation of 7-but-2-ynyl-8-chloro-3-methyl-1-(4-methyl-quinazolin-2-ylmethyl)-3,7-dihydro-purine-2,6-dione (12)

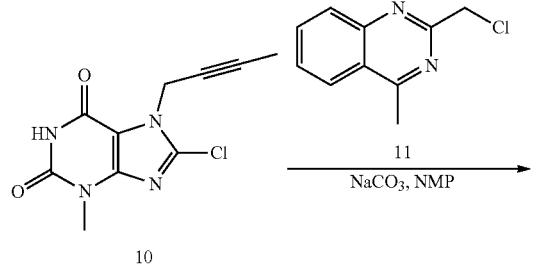

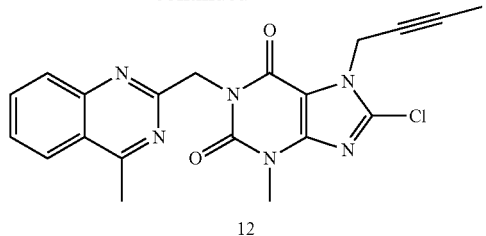

A total of 23.4 g of 7-but-2-ynyl-8-chloro-3-methyl-3,7-dihydro-purine-2,6-dione (10), 18.2 g of 2-chloromethyl-4-methyl-quinazoline (11), 10.8 g of Na$_2$CO$_3$ and 70 mL of NMP was added into a 250 mL three-necked round-bottomed flask. The resulting reaction mixture was heated to 100° C. and stirred for 4 h, then cooled down to 60° C. A total of 140 mL of EtOH and 140 mL of H$_2$O was mixed together and added to the reaction mixture slowly in 20 min, followed by addition of 11.2 g of acetic acid. The resulting suspension was stirred at 60° C. for 30 min, then cooled down to 25° C. and stirred for another 30 min. The product was collected by filtration, washed with a mixture of 45 mL of water and 45 mL of EtOH, dried under vacuum. A total of 29.3 g (yield 78%) of Compound 12 was obtained as white solid with 91.2% HPLC purity. $^1$H NMR (500 MHz, DMSO-$d_6$): δ 8.25 (d, 1H, J=8.5 Hz), 7.92 (t, 1H, J=8.0 Hz), 7.81 (d, 1H, J=8.5 Hz), 7.68 (t, 1H, J=7.5 Hz), 5.35 (s, 2H), 5.14 (d, 2H, J=2.0 Hz), 3.43 (s, 3H), 2.89 (s, 3H), 1.79 (s, 3H); $^{13}$C NMR (125 MHz, DMSO-$d_6$): δ 169.50, 160.87, 153.94, 151.06, 149.49, 147.49, 138.73, 134.66, 128.33, 127.74, 126.24, 123.00, 107.19, 82.51, 72.62, 46.28, 36.05, 30.10, 22.06, 3.46; Mass (m/z): 409.1 (M+H)$^+$.

Example 4: Preparation of Linagliptin

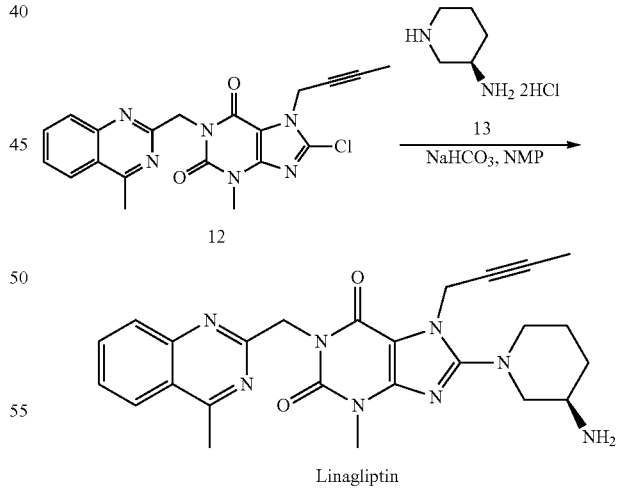

A total of 10.0 g of 7-but-2-ynyl-8-chloro-3-methyl-1-(4-methyl-quinazolin-2-ylmethyl)-3,7-dihydro-purine-2,6-dione (12), 5.1 g of (R)-3-aminopiperidine dihydrochloride (13), 30 mL of NMP and 7.2 g of sodium bicarbonate was added into a 250 mL three-necked round-bottomed flask. The reaction mixture was heated to 90° C. and stirred for 2 h, then cooled down to 40° C. Then, a total of 90 mL of dichloromethane (DCM) and 90 mL of water were charged, and the reaction mixture was stirred for 25 min. The organic phase was collected and the aqueous phase was extracted with another 30 mL of DCM. The combined organic phase was washed with 90 mL of $H_2O$ for 3 times (each washing takes no less than 20 min) and then stirred with 122.9 g of acetic acid solution (2.4 wt % in water) for 30 min. To the collected aqueous phase was charged with 120 mL of DCM and 49 mL of 1 N aq. NaOH solution. The resulting mixture was stirred for 30 min. The organic phase was collected and concentrated to dryness. The resulting yellow crude product was suspended in 30 mL of toluene and heated to reflux and stirred for 1 h. Then it was cooled down to 70° C. and stirred for 1 h. Next, it was cooled down to 50° C. slowly and stirred for 1 h. Finally, it was cooled down to 25° C. slowly and stirred for 2 h. The product was collected by filtration and dried under vacuum. A total of 8.9 g (yield 77%) of Linagliptin was obtained as pale yellow solid with 99.2% HPLC purity. $^1$H NMR (500 MHz, DMSO-$d_6$): δ 8.22 (d, 1H, J=8.0 Hz), 7.89 (m, 1H), 7.80 (d, 1H, J=8.5 Hz), 7.68 (m, 1H), 5.32 (s, 2H), 4.90 (s, 2H), 3.59-3.67 (m, 2H), 3.00 (m, 1H), 2.88 (s, 3H), 2.81-2.85 (m, 1H), 2.74-2.78 (m, 1H), 1.78-1.88 (m, 5H), 1.59-1.66 (m, 3H), 1.20-1.27 (m, 1H); $^{13}$C NMR (125 MHz, DMSO-$d_6$): δ 168.78, 160.97, 156.11, 153.20, 150.90, 149.01, 147.71, 134.01, 127.83, 127.08, 125.67, 122.45, 103.17, 81.10, 73.74, 57.61, 49.54, 47.27, 45.53, 35.47, 33.23, 29.39, 23.28, 21.53, 3.05; Mass (m/z): 473.2 $(M+H)^+$.

Example 5: Preparation of
8-iodo-3-methyl-3,7-dihydro-purine-2,6-dione (14)

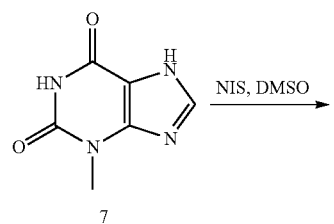

A total of 10.0 g of 3-methyl-3,7-dihydro-purine-2,6-dione (7), 17.9 g of NIS (N-iodosuccinimide) and 40 mL of DMSO was charged into the reactor. The resulting solution was stirred for 26 h at 40° C. A total of 60 mL of water was added dropwise. The resulting mixture was stirred at 40° C. for 30 min. The product was collected by filtration, washed with 40 mL of 1:1 DMSO+water and 40 mL of water respectively. It was then dried under vacuum. A total of 16.3 g (yield 91%) of Compound 14 was obtained as yellow solid with 94% HPLC purity. $^1$H NMR (500 MHz, $D_2O$): δ 2.69 (s, 3H); $^{13}$C NMR (125 MHz, $D_2O$): δ 164.05, 156.11, 150.53, 118.40, 100.61, 27.40; Mass (m/z): 292.9 $(M+H)^+$.

Example 6: Preparation of 7-but-2-ynyl-8-iodo-3-methyl-3,7-dihydro-purine-2,6-dione (16)

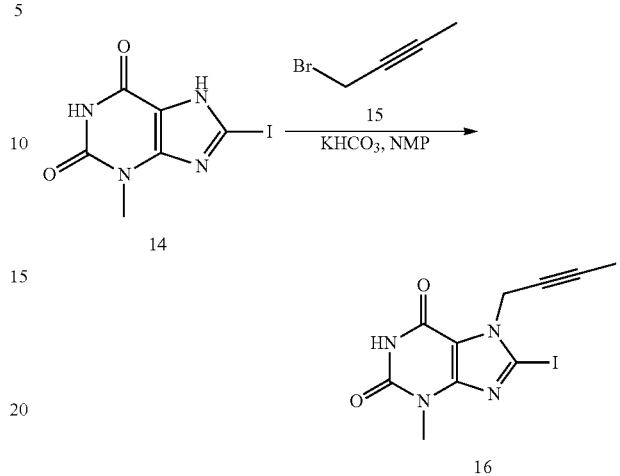

A total of 7.2 g of 8-iodo-3-methyl-3,7-dihydro-purine-2,6-dione (14), 3.0 g of $KHCO_3$ and 60 mL of NMP was charged to a 250 mL round-bottomed flask. The reaction mixture was heated to 55° C. A solution of 3.93 g of 1-bromo-2-butyne (15) in 10 mL of NMP was added dropwise. The reaction mixture was stirred at 55° C. for 2 h. A total of 70 mL of water was charged into the reaction mixture. The reaction mixture was stirred at 60° C. for 20 min. The product was collected by filtration and dried under vacuum. A total of 8.3 g (yield 97%) of Compound 16 was obtained as white solid with 98.0% HPLC purity. $^1$H NMR (500 MHz, DMSO-$d_6$): δ 11.26 (s, 1H), 5.00 (d, 1H, J=2.5 Hz), 3.31 (s, 3H), 1.80 (t, 3H, J=2.5 Hz); $^{13}$C NMR (125 MHz, DMSO-$d_6$): δ 153.55, 150.69, 109.08, 104.50, 81.90, 72.62, 28.51, 2.90; Mass (m/z): 345.0 $(M+H)^+$, 366.9 $(M+Na)^+$.

Example 7: Preparation of 7-but-2-ynyl-8-iodo-3-methyl-1-(4-methyl-quinazolin-2-ylmethyl)-3,7-dihydro-purine-2,6-dione (17)

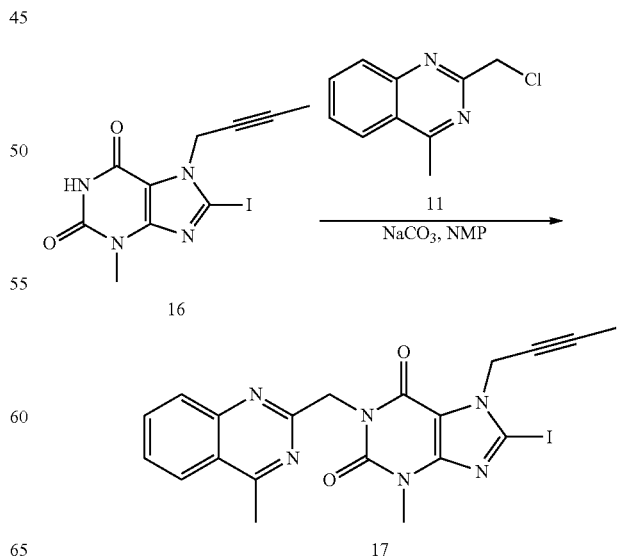

A total of 6.88 g of 7-but-2-ynyl-8-iodo-3-methyl-3,7-dihydro-purine-2,6-dione (16), 2.33 g of Na$_2$CO$_3$, 3.85 g of 2-chloromethyl-4-methyl-quinazoline (11) and 20 mL of NMP was charged into a 250 mL three-necked round-bottomed flask. The reaction mixture was heated to 90° C. and stirred for 11 h. A total of 40 mL of EtOH was added, followed by addition of 40 mL of water and 2.4 g of acetic acid. The resulting suspension was cooled down to 60° C. and stirred for 0.5 h. It was then cooled down to 25° C. The product was collected by filtration and dried under vacuum. A total of 6.52 g (yield 65%) of Compound 17 was obtained as pale yellow solid with 97% HPLC purity. $^1$H NMR (400 MHz, DMSO-d$_6$): δ 8.25 (d, 1H, J=7.5 Hz), 7.91 (m, 1H), 7.81 (d, 1H, J=8.0 Hz), 7.68 (m, 1H), 5.34 (s, 2H), 5.06 (s, 2H), 3.43 (s, 3H), 2.88 (s, 3H), 1.79 (t, 3H, J=2.4 Hz); $^{13}$C NMR (100 MHz, DMSO-d$_6$): δ 169.50, 160.95, 153.54, 151.12, 150.02, 149.46, 134.64, 128.34, 127.73, 126.26, 122.99, 109.10, 106.06, 82.38, 73.23, 46.24, 39.02, 30.03, 22.07, 3.50; Mass (m/z): 501.0 (M+H)$^+$.

Example 8: Preparation of Linagliptin

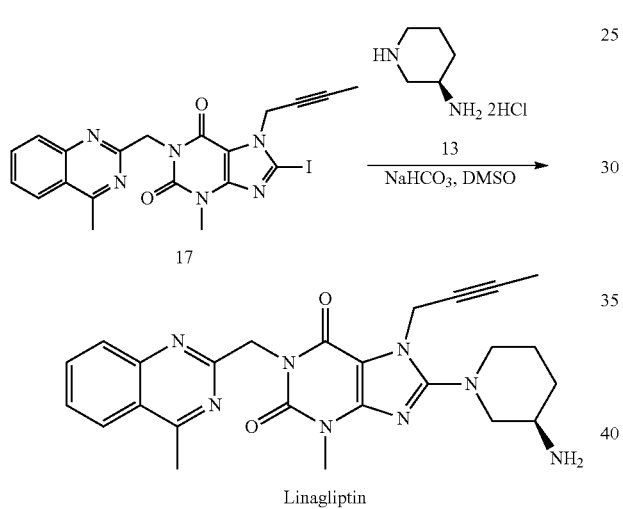

A total of 5.0 g of 7-but-2-ynyl-8-iodo-3-methyl-1-(4-methyl-quinazolin-2-ylmethyl)-3,7-dihydro-purine-2,6-dione (17), 1.9 g of (R)-3-aminopiperidine dihydrochloride (13), 15 mL of DMSO and 2.77 g of NaHCO$_3$ was charged into a three-necked round-bottomed flask. The mixture was heated to 110° C. and stirred for 4 h, then cooled down to 40° C. A total of 45 mL of water was added, followed by addition of 45 mL of dichloromethane. The mixture was stirred for 15 min. The organic phase was collected and the aqueous phase was extracted with 30 mL of dichloromethane. The combined organic phases was washed with 20 mL of water, then concentrated to dryness. The crude product was purified by column chromatography. A total of 2.53 g (yield 54%) of Linagliptin was obtained as pale yellow solid with 99.0% purity. $^1$H NMR (500 MHz, DMSO-d$_6$): δ 8.22 (d, 1H, J=8.0 Hz), 7.89 (m, 1H), 7.80 (d, 1H, J=8.5 Hz), 7.68 (m, 1H), 5.32 (s, 2H), 4.90 (s, 2H), 3.59-3.67 (m, 2H), 3.00 (m, 1H), 2.88 (s, 3H), 2.81-2.85 (m, 1H), 2.74-2.78 (m, 1H), 1.78-1.88 (m, 5H), 1.59-1.66 (m, 3H), 1.20-1.27 (m, 1H); $^{13}$C NMR (125 MHz, DMSO-d$_6$): δ 168.78, 160.97, 156.11, 153.20, 150.90, 149.01, 147.71, 134.01, 127.83, 127.08, 125.67, 122.45, 103.17, 81.10, 73.74, 57.61, 49.54, 47.27, 45.53, 35.47, 33.23, 29.39, 23.28, 21.53, 3.05; Mass (m/z): 473.2 (M+H)$^+$.

The invention claimed is:

1. A method for preparing a compound of formula (I*):

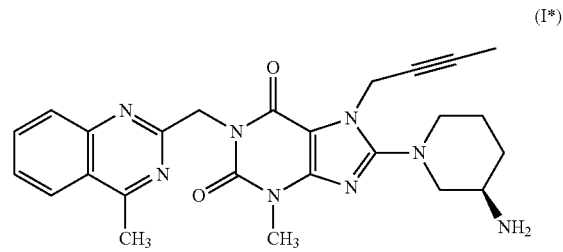 [SMILES: CC#CCn1c(N2CCC[C@@H](N)C2)nc2c1c(=O)n(Cc1nc(C)c3ccccc3n1)c(=O)n2C]

(I*)

the method comprising the following step:
reacting a compound of formula (II):

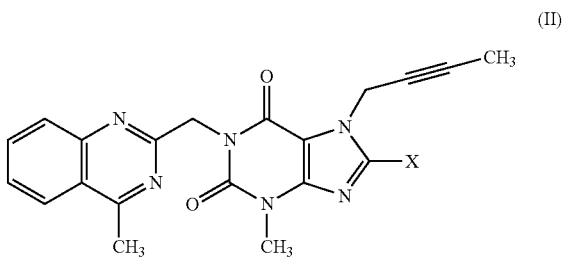

(II)

wherein:
X is chloro or iodo;
with (R)-3-aminopiperidine of formula (III):

(III)

or a pharmaceutically acceptable salt thereof,
in the presence of a polar aprotic solvent and a base, to form the compound of formula (I*) above.

2. The method according to claim 1, wherein the pharmaceutically acceptable salt of (R)-3-aminopiperidine of formula (III) is:

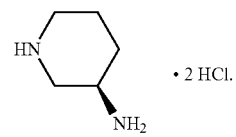

3. The method according to claim 1, wherein the base is sodium carbonate, potassium carbonate, sodium bicarbonate or potassium bicarbonate.

4. The method according to claim 1, wherein the polar aprotic solvent is N-methyl-2-pyrrolidone, dimethylsulfoxide, N,N-dimethylacetamide or N,N-dimethylformamide.

5. The method according to claim 1, wherein X is chloro.

6. The method according to claim 1, wherein X is iodo.

7. The method according to claim 1, wherein X is chloro, the base is sodium bicarbonate and the polar aprotic solvent is N-methyl-2-pyrrolidone.

8. The method according to claim 1, wherein X is iodo, the base is sodium bicarbonate and the polar aprotic solvent is dimethylsulfoxide.

9. The method according to claim 1, wherein the reaction is conducted at a temperature in the range selected from the group consisting of 20° C. to 120° C. and 40° C. to 110° C.

* * * * *